United States Patent
Fontana

(10) Patent No.: US 10,639,661 B2
(45) Date of Patent: May 5, 2020

(54) DEVICE OF A WEARABLE TYPE FOR DISPENSING A FLUID, AND CORRESPONDING DISPENSING METHOD

(71) Applicant: STMICROELECTRONICS S.r.l., Agrate Brianza (MB) (IT)

(72) Inventor: Fulvio Vittorio Fontana, Monza (IT)

(73) Assignee: STMICROELECTRONICS S.R.L., Agrate Brianza (MB) (IT)

( * ) Notice: Subject to any disclaimer, the term of this patent is extended or adjusted under 35 U.S.C. 154(b) by 934 days.

(21) Appl. No.: 14/867,099

(22) Filed: Sep. 28, 2015

(65) Prior Publication Data

US 2016/0184852 A1  Jun. 30, 2016

(30) Foreign Application Priority Data

Dec. 29, 2014 (IT) .............................. TO2014A1114
Jul. 2, 2015 (IT) ........................ 102015000030162

(51) Int. Cl.
  *B05B 12/08* (2006.01)
  *B05B 15/62* (2018.01)
  (Continued)

(52) U.S. Cl.
  CPC ....... *B05B 12/085* (2013.01); *A61M 5/14224* (2013.01); *A61M 5/14248* (2013.01);
  (Continued)

(58) Field of Classification Search
  CPC ........... A61M 2005/14268; A61M 2205/0244; A61M 5/14224; A61M 5/14248;
  (Continued)

(56) References Cited

U.S. PATENT DOCUMENTS 5,205,819 A   4/1993  Ross et al.
8,298,183 B2  10/2012 Menot et al.
(Continued)

FOREIGN PATENT DOCUMENTS

CN  101641522 A  2/2010
CN  201431672 Y  3/2010
(Continued)

OTHER PUBLICATIONS

Dong Xia, "A Bionic Artificial Heart Blood Pump Driven by Permanent Magnet Located Outside Human Body", IEEE Transactions on Applied Superconductivity, vol. 22, No. 3, Jun. 2012 , pp. 1-4.

*Primary Examiner* — Jason E Flick
(74) *Attorney, Agent, or Firm* — Slater Matsil, LLP

(57) ABSTRACT

A device for dispensing a fluid includes a fixed part to be worn by a user, a fluid connection including a terminal outlet, a needle coupled to the terminal outlet of the fluid connection for dispensing a fluid, and a replaceable part coupled to the fixed part via the fluid connection. The replaceable part includes a reservoir for containing the fluid to be dispensed, and a micro-pump coupled to the reservoir to send the fluid to the fixed part through the fluid connection. An actuator operates the micro-pump. The fixed part includes a pressure-sensor in proximity to the terminal outlet of the fluid connection and is associated with dispensing the fluid from the needle. An electronic control module controls operation of the micro-pump via the pressure-sensor.

23 Claims, 16 Drawing Sheets

(51) Int. Cl.
*A61M 5/168* (2006.01)
*A61M 5/142* (2006.01)
*B05B 11/00* (2006.01)

(52) U.S. Cl.
CPC ..... *A61M 5/16854* (2013.01); *B05B 11/3042* (2013.01); *B05B 15/62* (2018.02); *A61M 2005/14268* (2013.01); *A61M 2205/0244* (2013.01)

(58) Field of Classification Search
CPC .............. A61M 5/16854; A61M 5/142; A61M 5/14244; A61M 5/14212; A61M 5/16831; A61M 5/168; B05B 11/3042; B05B 12/085; B05B 15/061; B05B 15/62
USPC ...................................................... 604/890.1
See application file for complete search history.

(56) References Cited

U.S. PATENT DOCUMENTS

| | | | |
|---|---|---|---|
| 2004/0204673 A1* | 10/2004 | Flaherty ............ | A61M 5/14248 604/65 |
| 2008/0230035 A1 | 9/2008 | Inoue | |
| 2010/0331826 A1 | 12/2010 | Field et al. | |
| 2011/0021993 A1 | 1/2011 | Bar-Haim et al. | |
| 2011/0060280 A1* | 3/2011 | Caffey .............. | A61M 5/14248 604/151 |

FOREIGN PATENT DOCUMENTS

| | | |
|---|---|---|
| CN | 101900141 A | 12/2010 |
| CN | 202250753 U | 5/2012 |
| CN | 205592112 U | 9/2016 |
| JP | 2008232099 A | 10/2008 |

* cited by examiner

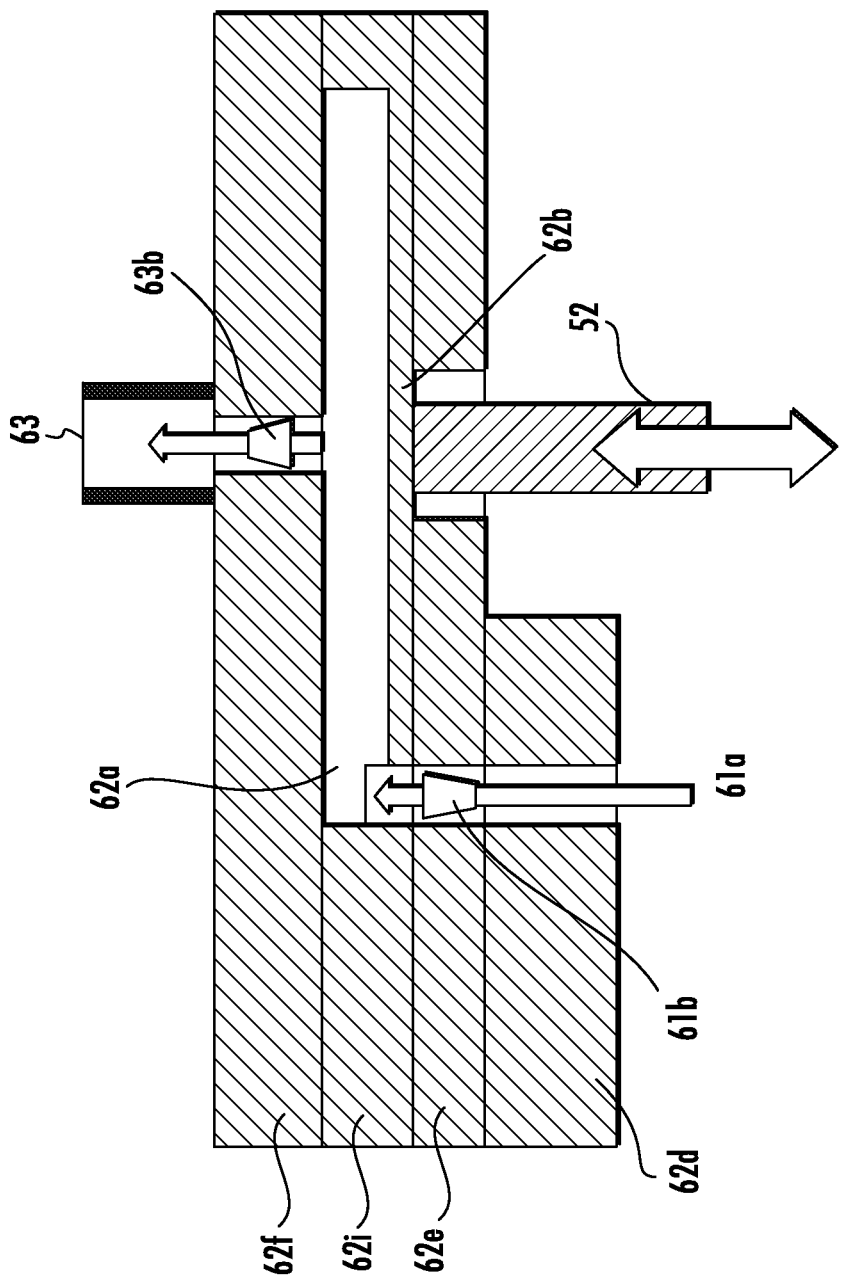

DEVICE OF A WEARABLE TYPE FOR DISPENSING A FLUID, AND CORRESPONDING DISPENSING METHOD

FIELD OF THE INVENTION

The present disclosure relates to a device of a wearable type for dispensing a fluid. The device includes a fixed part worn by a subject and a replaceable part associated with the fixed part via a fluid connection. The replaceable part includes a reservoir for containing the fluid to be dispensed and a micro-pump for sending the fluid to the fixed part through the fluid connection. The fixed part includes an electronic control module configured for controlling operation of the micro-pump. The device includes a battery actuator for operating the micro-pump.

Various embodiments may be applied to devices for dispensing fluids containing insulin or other medicinal preparations.

BACKGROUND

There are devices for dispensing fluids that contain, for example, insulin or other medicinal preparations, which can be worn by a user or patient so as to enable dispensing of the fluid continuously or when necessary.

For these types of devices, it is very important to implement control of the flow of the fluid medicine continuously in order to guarantee effectiveness of treatment and safety of the patient in the event of any malfunctioning, such as leaks, air bubbles, occlusions, etc.

There are known systems for this purpose made up of two parts. A fixed part includes the electronic-control part, the memory, and the radio frequency interface, and can, for example, be worn by the user. A replaceable part includes the reservoir for the medicine, the micro-pump of a MEMS (microelectromechanical system) type, with the corresponding actuator and the battery that supplies the actuator.

In greater detail, in this connection, FIG. 1 illustrates a device for dispensing a fluid 10 that comprises a replaceable part 20, which in turn comprises a reservoir 21, a MEMS micro-pump 22 which receives through an inlet duct 21a the fluid from the reservoir 21, and is associated to a pressure sensor 23. The device 10 also includes an actuator 24 and a battery 25. A fixed part 30 comprises an electronic control module 31, which in turn comprises a memory 32 and a communication interface operating at a radio frequency 33.

Designated by 11 is a signal connection between the pressure sensor 23 and the electronic module 31, whereas designated by 12 is a fluid dispensing conduit that from the micro-pump 22, through the fixed part 31, reaches a dispensing needle 13 for dispensing the fluid medicine into the body of the subject who is wearing the fluid-dispensing device 10.

Designated by 26 is a terminal of the actuator 24, for example, the shaft or punch of a linear actuator, which operates the micro-pump 22. The micro-pump 22 in general comprises a pumping chamber, the top wall of which is constituted by a membrane. The terminal 26 periodically exerts mechanical pressure on the membrane of the pump 22.

Control of the flow is carried out via control of the pumping pressure on the MEMS micro-pump, via the pressure sensor (or sensors) 23 present on the MEMS micro-pump 22.

The signal of the pressure sensor 23 is transferred to the substrate of the micro-pump 22 via wire bonding or by a connection of some other type (microjunctions obtained by remelting of a soldering alloy pre-deposited on the MEMS, or by dispensing conductive glue, or by thermosonic remelting of the contacts of the micro-pump on those of the substrate). From the substrate of the micro-pump the pressure signals are transferred, on the signal connection 11, to the electronic-control part 31 on the fixed part 30. This implements signal connection 11 via sliding contacts or spring contacts.

As illustrated in FIG. 1A, the micro-pump 22 comprises a pumping chamber 22a made up of three different silicon layers set on top of a silicon substrate 22d, of which the two extreme ones constitute a bottom layer 22e and a roof layer or lid 22f of the micro-pump 22, and which identify between them a chamber layer 22i, dug in which is the pumping chamber 22a. The inlet duct 21a and the outlet towards the fluidic or fluid dispensing conduit 12 must be arranged on the bottom layer 22e of the micro-pump 22 in order to be able to interface the substrate 22d since the structure of the two valves, 21b on the inlet duct 21a and 12b on the outlet represented by the fluid dispensing conduit 12, entails that these cannot be made on a single silicon layer, but must, instead, each be made on a different layer, the bottom layer 22e and the top layer 22f. Consequently, the process is aimed at obtaining that the outlet circuit from the pumping chamber 22a passes through the roof layer 22f and is then brought back onto the bottom layer 22e by forming a channel 22g on the roof layer 22f, which is sealed via a lid element 22h.

The above device presents some drawbacks in so far as the architecture, in particular with respect to the replaceable part which is complex, and the arrangement of the pressure sensor which requires arrangement inside the MEMS micro-pump of circuits and bonding pads. Furthermore, such an arrangement involves channels made on the surface of the pump or in a layer where the pump itself is provided.

SUMMARY

The pressure-sensor means or pressure sensor may be arranged in the fixed part in the proximity of a terminal outlet part of the fluid connection, associated with a dispensing needle.

The fixed part may comprise the actuator and the device to be worn by a user, and may comprise a member for transmission of motion that connects the actuator in the fixed part to the micro-pump in the replaceable part.

The transmission member may be in the form of a lamina or strap, and in particular, made of steel. The lamina may be associated in a permanent way to the micro-pump and may be inserted for engagement with the actuator.

The actuator may be a cantilever actuator, for example. The actuator may also be a linear actuator.

The engagement means or engagement system may comprise a low-friction pressing element pushed by a spring against a surface of the lamina, with the other surface of the lamina resting on the actuator, and in particular, an end part of the cantilever of the actuator.

The engagement system may comprise a permanent magnet pushed by a spring against a surface of the lamina, with the other surface of the lamina resting on the actuator, and in particular, an end part of the cantilever of the actuator.

The outlet of the fluid connection of the micro-pump installed on the replaceable part may be connected to the hydraulic circuit of the fixed part via a needle system installed on the fixed part that perforates a fluid-tight diaphragm on the replaceable part.

The outlet conduit (of the micro-pump installed on the replaceable part) may be located on a wall opposite to a fluid connection that conveys the fluid from the reservoir to the micro-pump.

Another aspect is directed to a method for control of the flow in a wearable device for dispensing a fluid of the type described, where control of the fluid may be a function of the drop in pressure measured by the pressure sensor on the dispensing conduit downstream of the replaceable part. In particular, this may be downstream of the conduit with the outlet valve, namely, in the proximity of the attachment of the fluid conduit with the dispensing needle.

BRIEF DESCRIPTION OF THE DRAWINGS

Various embodiments will now be described, purely by way of example, with reference to the annexed figures, wherein:

FIG. 2A shows a principle diagram of an embodiment of a micro-pump that can be used in the device for dispensing the fluid of FIG. 2;

DETAILED DESCRIPTION

In the ensuing description, numerous specific details are provided in order to enable a better understanding of the embodiments provided by way of example. The embodiments may be implemented with or without specific details, or else with other methods, components, materials, etc. In other circumstances, well-known structures, materials, or operations are not illustrated or described in detail so that various aspects of the embodiments will not be obscured. Reference in the course of this description to "an embodiment" or "one embodiment" is meant to indicate that a particular detail, structure, or characteristic described in connection with the embodiment is comprised in at least one embodiment. Hence, recurrence of phrases such as "in an embodiment" or "in one embodiment" that may appear in various points in the course of the present description do not necessarily refer to one and the same embodiment.

Furthermore, the particular features, structures, or peculiarities may be combined in any convenient way in one or more embodiments. The references are provided herein only for convenience of the reader and do not define the scope or the meaning of the embodiments.

Figure 2:
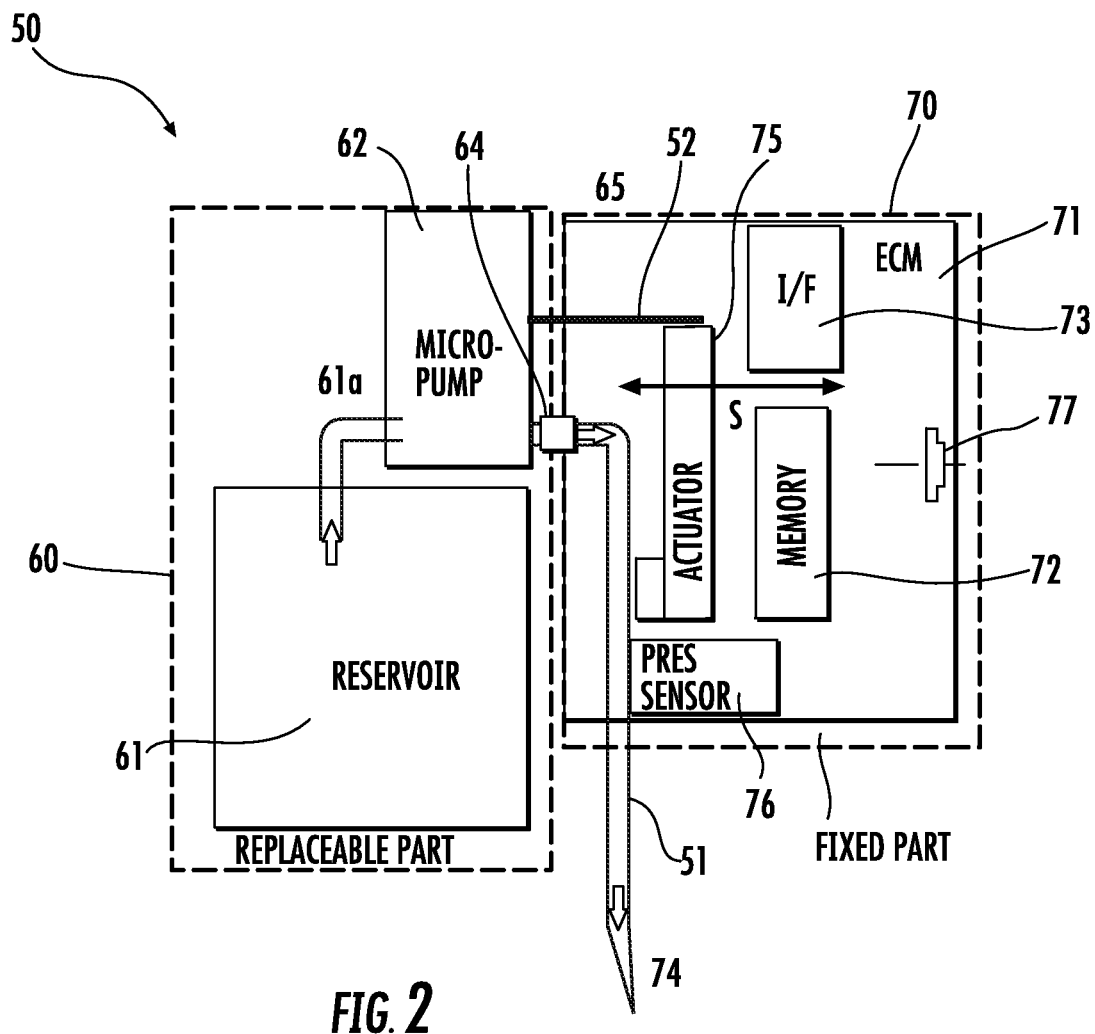
FIG. 2 shows a principle diagram of a device for dispensing a fluid.

The above device 50 is illustrated in FIG. 2, where a replaceable part 60 comprises a reservoir 61 and a MEMS micro-pump 62. A fixed part 70 comprises, instead, an electronic module 71 including a memory 72 and a communication interface 73 operating at a radio frequency, an actuator 75, in particular a piezo-actuator, a pressure sensor 76, and a rechargeable battery 77 for supplying the actuator 75 autonomously.

The replaceable part 60 is connected to the fixed part 70 by connecting an outlet conduit 64 thereof to a fluid connection that conveys the fluid to the dispensing needle 74, i.e., a fluidic or fluid dispensing conduit 51. In addition, a member for transmission of motion 52, in particular a metal lamina or strap, preferably made of steel, connects the piezo-actuator 75 to the micro-pump 62. The fixed part further comprises (not illustrated in FIG. 2) acoustic and visual alarms, and a temperature sensor. The fluid dispensing conduit 51 is set in the fixed part 70, and the replaceable part 60 sets itself in fluid connection with the fixed part 70 via a conduit with an outlet valve 64 that gives out onto the outside of the replaceable part 60 (with the modalities illustrated in what follows with reference, for example, to FIGS. 3A and 3B) and that comes from the micro-pump 62.

The pressure sensor 76 is set in the fixed part 70 so as to measure the pressure in the fluid dispensing conduit 51, as far downstream as possible towards the dispensing needle 74. This not only avoids the need for connections in the substrate of the micro-pump 62, but also enables configuration of the electronic module 71 for carrying out control of the fluid as a function of the drop in pressure measured by the pressure sensor 76 downstream of the connection between the fixed part 70 and the replaceable part 60. In particular, this is downstream of the conduit with the outlet valve 64, preferably, as has been said, in the proximity of the attachment of the fluid conduit 51 with the needle 74.

Control of the flow, which is once again carried out via a control of pressure using an absolute-pressure sensor 76 installed on the fixed part 70 immediately before the outlet of the fluid dispensing conduit 51 that conveys the fluid from the micro-pump 62, makes it possible to check, by measuring the drop in pressure, for any leakage at any point between the reservoir 61 of the fluid and the outlet. This includes the hydraulic connection between the replaceable part 60 and the fixed part 70.

Figure 1:
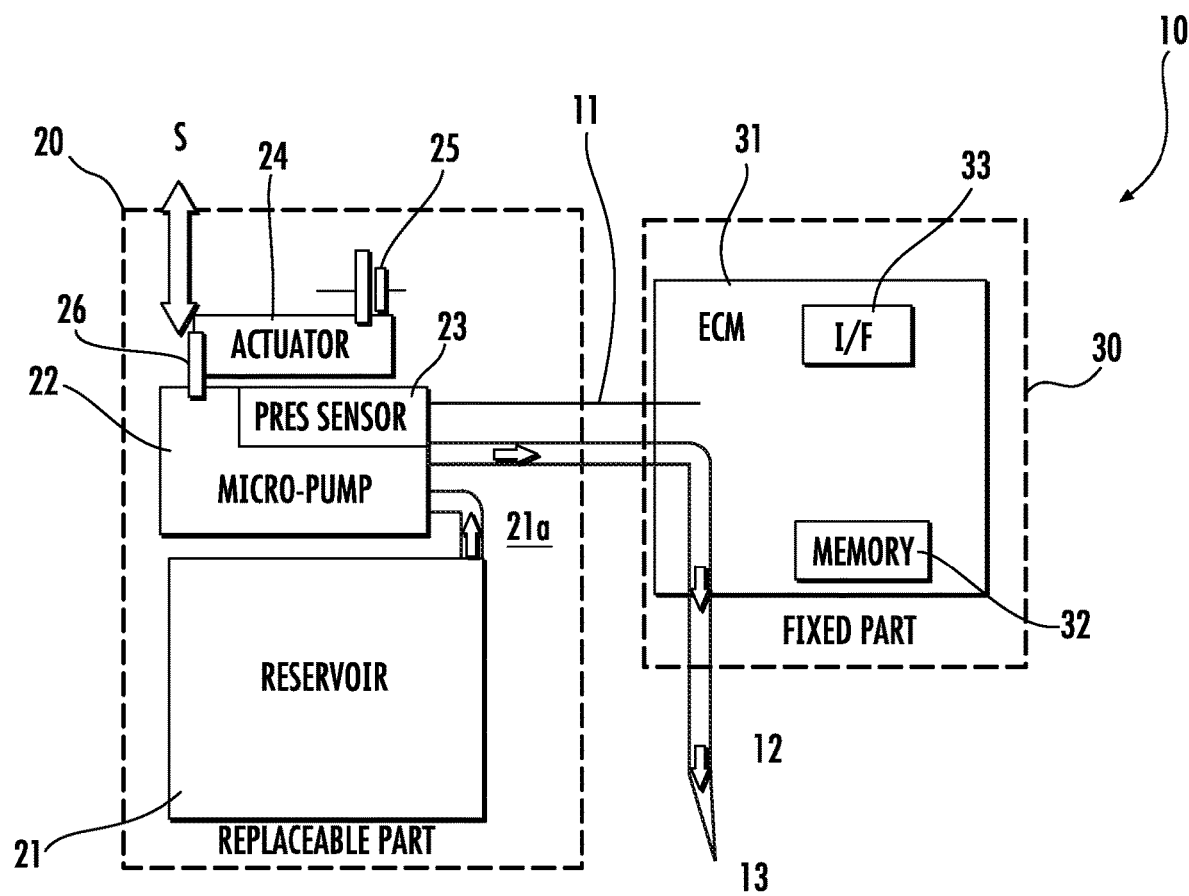
FIGS. 1 and 1A have been described previously.
Figure 1A:
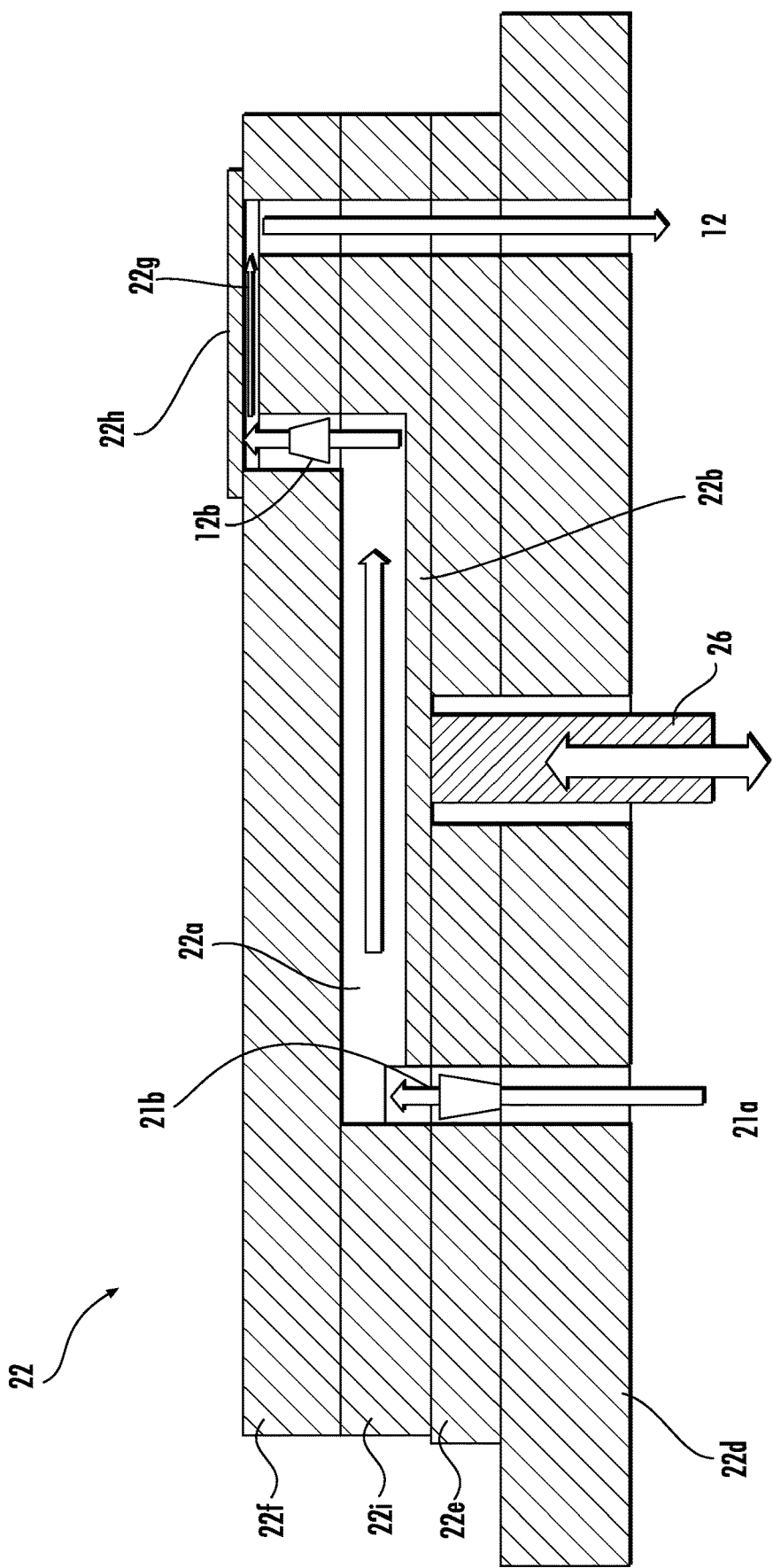

Elimination of the circuits in the substrate makes it possible to have the inlet (conduit 61a, which is also provided with an inlet valve 61b) and the outlet (conduit provided with an outlet valve 64) of the fluid on two opposite surfaces of the pump 62, specifically the substrate side and the membrane side, eliminating the need for channels (like the channel 22g of FIG. 1A) provided on the surface thereof and sealed with an outer lid, or else buried within a layer where the pump itself is provided.

Represented in this connection in FIG. 2A is a possible embodiment of the micro-pump 62. Like the pump 22 in FIG. 1A, the above micro-pump 62 comprises a pumping chamber 62a made with three different silicon layers, of which the two extreme ones constitute the bottom layer 62e and the roof layer 62f, which identify between them the chamber layer 62i, dug in which is the pumping chamber 62a. The inlet duct 61a, with a corresponding inlet valve 61b is arranged passing through the bottom layer 62e of the micro-pump 62 and the substrate layer 62d, whereas an outlet conduit 63 from the chamber 62a is set on the roof layer 62f that functions as a lid. This conduit is in general in flow continuity with the conduit 64 and can have an outlet valve 63b thereof made in the roof layer 62f or else can share this valve with the duct 64. It is thus not necessary to provide a channel on the lid layer, as in the case of FIG. 1A, that is then to be sealed. It is to be noted that the micro-pump 62 of FIG. 2A has the actuator 52 that operates through the substrate 62d of the inlet conduit 61a, whereas the outlet conduit 63 is located on the opposite side. Consequently, the fluid is then sent towards the face of the replaceable part 60 through further conduit segments. In FIG. 2 and in what follows the micropump 62 is instead represented schematically as having the outlet for the fluid on the same side as the point of application of the lamina or strap 52.

Figure 15:
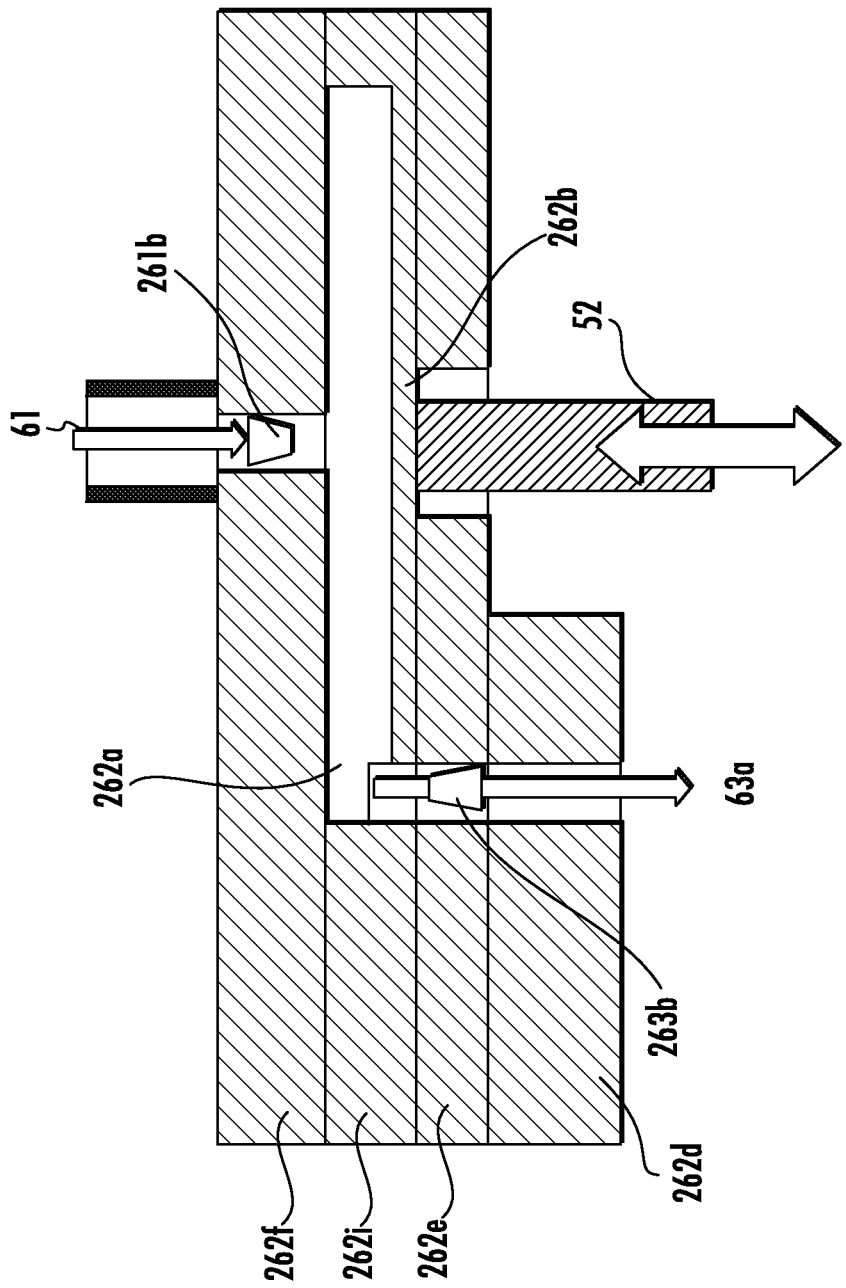
FIG. 15 shows a principle diagram of an alternative embodiment of a micro-pump used in the device for dispensing the fluid of FIG. 2.

In FIG. 15 it is shown instead a micro-pump 262 which includes a pumping chamber 262a made with three different silicon layers, of which the two extreme ones constitute the bottom layer 262e and the roof layer 262f, which identify between them the chamber layer 262i, in which is the pumping chamber 262a.

The inlet duct 261a, with a corresponding inlet valve 261b is arranged passing through the roof layer 262f of the micro-pump 262, whereas an outlet conduit 263 from the chamber 262a is set on the roof layer 262f and the substrate 262d. This conduit is in general in flow continuity with the conduit 64 and can have an outlet valve 263b thereof made in the bottom layer 262e or else can share this valve with the conduit 64. Also in this embodiment is thus not necessary to provide a channel on the lid layer, as in the case of FIG. 1A, that is then to be sealed.

The foregoing simplification of the architecture of the pump enables the latter to be obtained also with materials other than silicon, such as moulded plastic materials or else plastic resins coupled to a metal, ceramic, or glass substrate, the choice depending only upon the pumping precision, which reflects upon the tolerances of the process of manufacture of the pump.

The inlet and outlet valves and the pumping membrane, in addition to being made from a silicon layer with a process of subtraction, which is extensively used in MEMS technologies, may be obtained with plastic moulding, or else by including metal laminas in the plastic body.

Figure 3A:
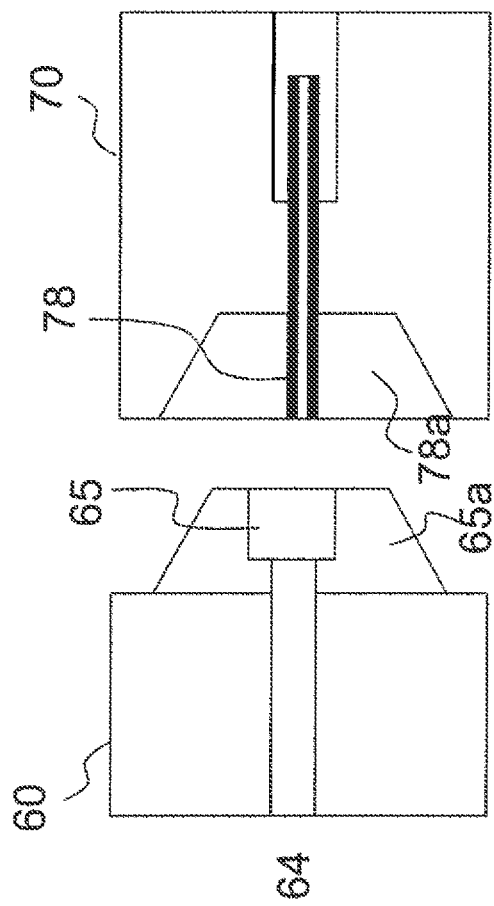
FIGS. 3A and 3B are schematic illustrations of a detail of a connection system of the device of FIG. 2.
Figure 3B:
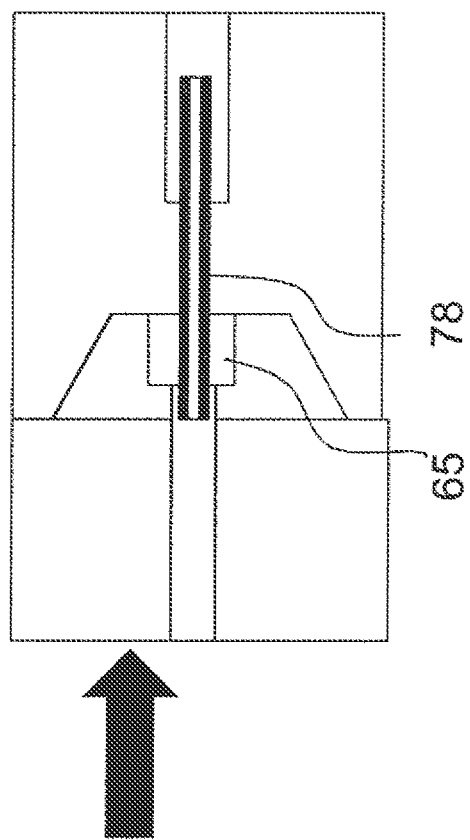

The conduit with the outlet valve 64 of the micro-pump 62 installed on the replaceable part 60 is connected to the hydraulic circuit, i.e., the fluid dispensing conduit 51, of the fixed part 70 via a needle system 78 installed on the fixed part 70 that perforates a fluid-tight diaphragm 65 on the replaceable part 60, as illustrated in FIGS. 3A and 3B, which show the replaceable part 60 and the fixed part 70 in a separate configuration prior to being coupled and in a coupled configuration, respectively. The needle 78 for the connection is shaped so as to prevent occlusion thereof during perforation of the diaphragm 65. The diaphragm 65 is in the front part of a conical protrusion 65a, while the needle system 78 comprises a seat 78a of a corresponding shape that houses the conical protrusion 65a in the coupled configuration. The material of the diaphragm 65 is silicon-based so as to be biologically compatible with the fluid dispensed by the pump 62.

The actuator 75 is of a piezoelectric type, and, as illustrated in FIG. 2, imposes a displacement S on the strap 52, substantially along its main axis, which coincides with an axis normal to the membrane of the micro-pump 62. As has been said, the actuator 75 is installed on the fixed part 70.

Figure 4:
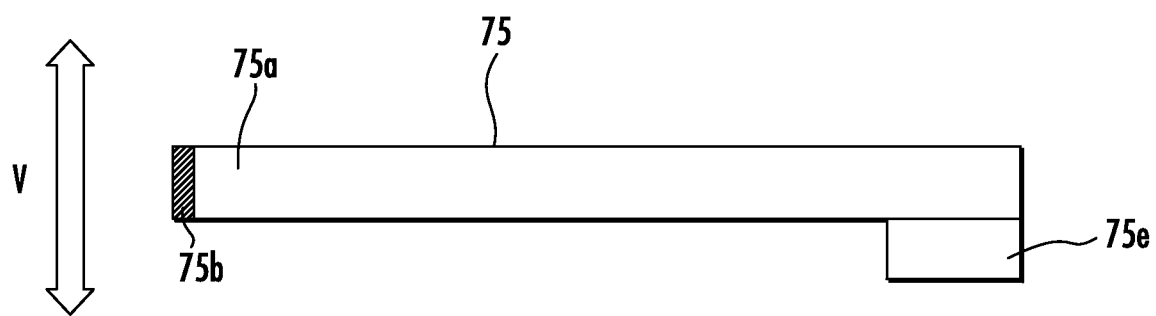
FIG. 4 is a schematic illustration of a first actuator used in the device of FIG. 2.

The above actuator 75, in one embodiment, may be of a cantilever type, as illustrated with reference to FIGS. 4, 5, and 6. As is known, a piezoelectric cantilever actuator comprises a base 75e, an arm, or a beam 75a, and an end portion 75b. A piezoelectric element between the base and the arm causes the arm 75a to oscillate vertically in the direction V about a resting position. As illustrated in FIG. 2, the cantilever actuator 75 is set in the fixed part 70 in such a way that the arm 75a is located in a resting position perpendicular to the displacement S and performs oscillations tangential to the displacement S (see also FIG. 7B); i.e., the direction V is parallel to the displacement S. In various embodiments, the actuator 75 may, instead, be a linear type, as illustrated, for example, in FIG. 10.

Figure 5:
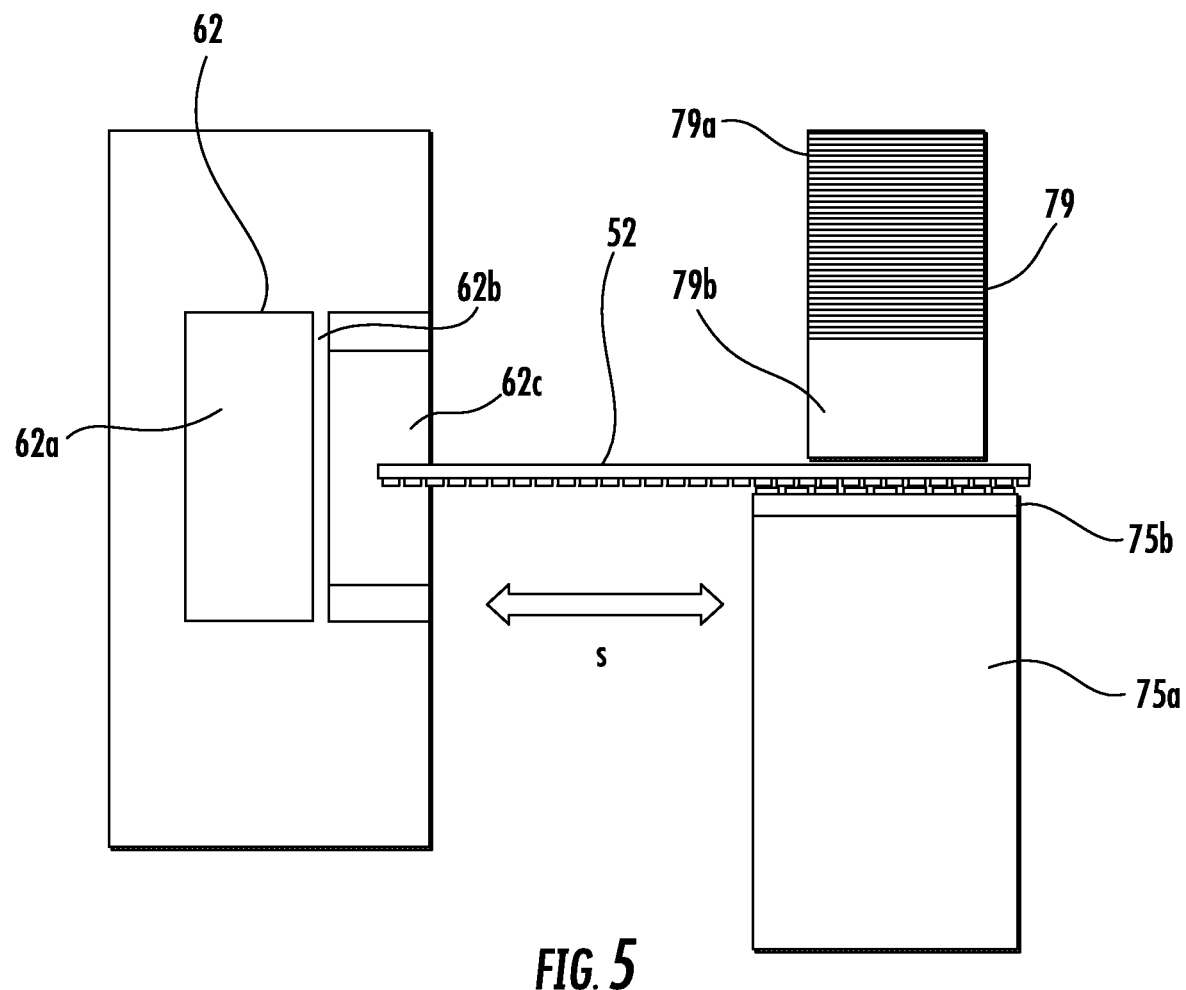
FIG. 5 is a schematic illustration of a first configuration of the device of FIG. 2, with a first system for engagement for transmitting motion.

The MEMS micro-pump 62 described, as has been mentioned, is of the volumetric type, in which a mobile element varies the volume of a chamber of the micro-pump; specifically, it is a membrane pump and is illustrated in FIG. 5. The micro-pump 62 comprises the pumping chamber 62a, one wall of which is represented by a silicon membrane 62b. The plane of the membrane 62b is perpendicular to the displacement S, and the membrane 62b of the pump 62 is actuated by the metal strap 52 that is associated thereto, for example, via gluing or welding. In FIG. 5 this connection is obtained by gluing 62c.

Moreover illustrated in FIG. 5 is the member for transmission of motion, which, as has been said, is a strap connection 52. The connection between the strap 52 and the actuator 75 depends upon the type of actuator 75. Illustrated in FIG. 5 is a connection of the strap 52 with the cantilever actuator 75, which is obtained via a lateral engagement system 79 capable of eliminating the sum of tolerances deriving from fixing of the piezoelectric actuator 75 on the fixed part 70. In particular, this is from coupling of the fixed part, plus the mobile part, plus the length of strap, fixing of the strap on the micro-pump.

It should be noted how the device 50 presents the strap 52 associated in a fixed way to the micro-pump 62, i.e., via gluing 62c or other means mentioned above, and can be inserted in means, for example, the engagement means 79, for engagement of the actuator 75. In other words, the replaceable part 60 carries the strap 52, which is engaged, at the moment of coupling to the actuator 75, on the fixed part 60.

The above lateral engagement system 79 is guaranteed by a spring-operated pressing element, comprising a spring 79a and a pusher 79b, which operate in the direction of the longitudinal axis of the arm 75a and in a direction perpendicular to the axis of the strap 52 and to the displacement S, and act on a top face of the strap 52. Coupling between the pressing element 79 and the upper side of the strap 52 has a low coefficient of friction. For, example, the pusher 79b is made of Teflon, and the strap 52 is made of steel so that the value of the coefficient of friction is 0.005. The pusher 79b presses the strap 52 against the mobile end 75b, which is preferably coated with copper or plastic material or has mounted thereon a terminal made of plastic material, of the piezoelectric actuator 75. This coupling between the underside of the strap 52 and the mobile end 75b of the piezoelectric actuator has, instead, a high coefficient of friction. In this way, the motion of the end 75b of the piezoelectric actuator 75 is transmitted to the strap 52, which slides on the spring-operated pressing element 79.

By way of example, the spring 79a can be obtained with a 0.5-mm metal wire, have an external diameter of 5 mm and a length of 15 mm. The coefficient of friction between steel and copper is 1.0. The pressing element 79 exerts, for example, a force greater than 2 N, and the actuator 75 exerts a maximum force of 2 N in the direction of displacement S. The pressure of the fluid exiting from the micro-pump 62 is, for example, 100 kPa.

FIG. 6 shows the steps of coupling and operation of the fixed part 70 and of the replaceable part 60, with respect to the member for transmission of motion, i.e., the strap 52.

Figure 6A:
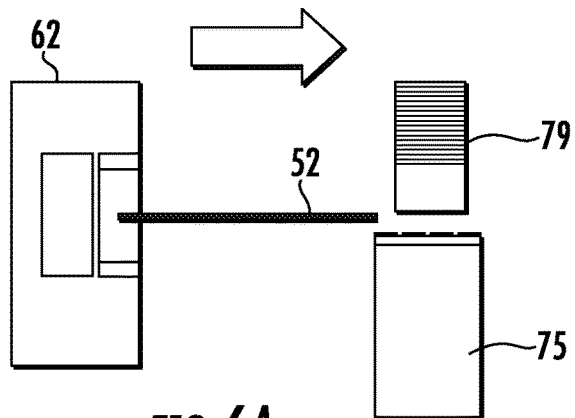
FIG. 6A-6D are schematic illustrations of steps of engagement and operation of the device in the first configuration of FIG. 5.
Figure 6B:
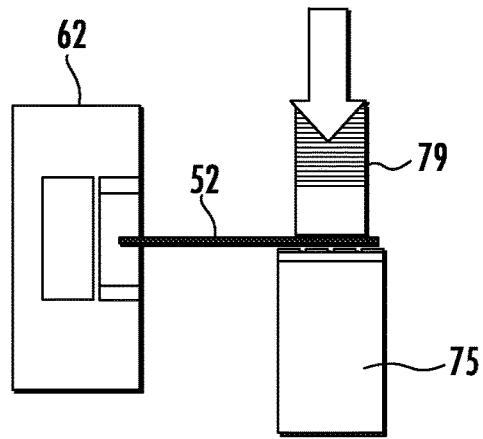
Figure 6C:
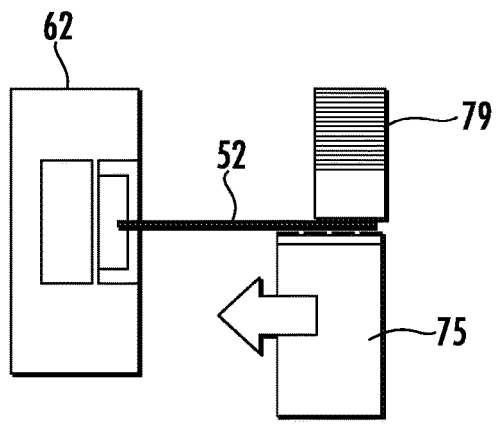
Figure 6D:
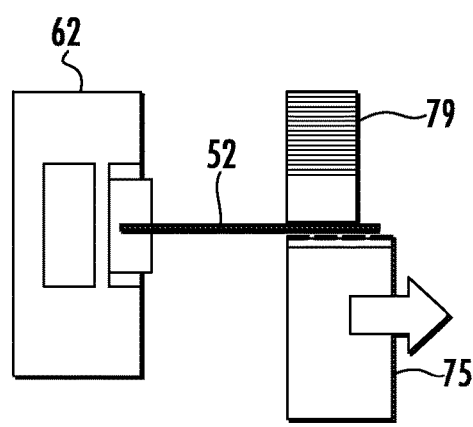

Illustrated in FIG. 6A is a step of insertion of the strap 52, which is glued to the membrane 62b, between the end 75b and the pusher 79b at the start of coupling between the two parts 60 and 70. Illustrated in FIG. 6B is a step in which the pressing element 79 is brought to exert, via the spring 79a, operated by a lever mechanism (not illustrated), accessible, for example, manually by the user on the outside of the fixed part 70, a force on the upper side of the strap 52 that presses the latter against the end 75b of the actuator 75. Illustrated in FIG. 6C is a pumping step, in which the arm of the actuator 75 presents a movement, linearized in FIG. 7A, of thrust towards the membrane 62b in the direction of displacement S oriented from the fixed part 70 towards the replaceable part 60, which pushes the strap 52 in the same direction, while the pressing element 79 slides in the opposite direction. Instead, illustrated in FIG. 6D is a suction step, in which the arm 75a of the actuator 75 presents a drawing motion in regard to the membrane 62b in the direction of displacement S oriented from the replaceable part 60 towards the fixed part 70, which pulls the strap 52 in the same direction, while the pressing element 79 slides in the opposite direction.

Figures 7A, 7B:
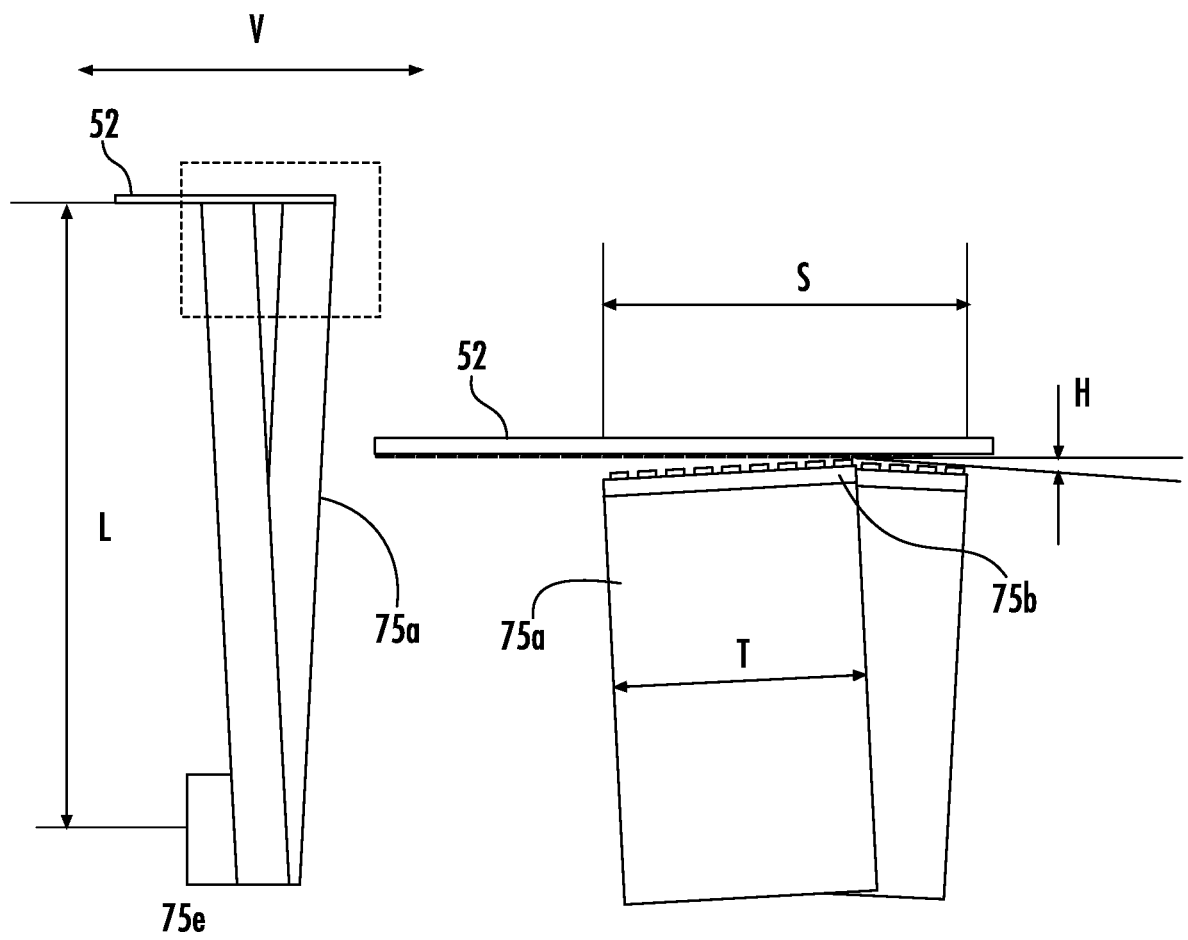
FIGS. 7A and 7B are schematic illustrations of quantities involved in operation of the actuator of FIG. 4.

Illustrated in FIGS. 7A and 7B is a detailed side view of the actuator 75 coupled to the strap 52. A free length L of the arm 75a must be much longer than the absolute displacement of the end 75a of the actuator so as to be able to minimize a displacement along the perpendicular axis of motion of the actuator, thus preventing a reduction in the force of contact with the strap. For instance, the displacement S is comprised between 20 and 50 μm, whereas the free length L is comprised between 5,000 and 10,000 μm.

With reference to FIG. 7B, which shows in detail the end 75a appearing in FIG. 7A, H is the displacement perpendicular to the direction of motion S, while T is the thickness of the arm 75a at rest in the direction parallel to the direction of motion. Hence, H=T arctan (S/L).

Consequently, given the values of thickness T and displacement S, the length L must be increased to minimize the perpendicular displacement H and to guarantee the contact with the strap 52 during motion.

Figure 8:
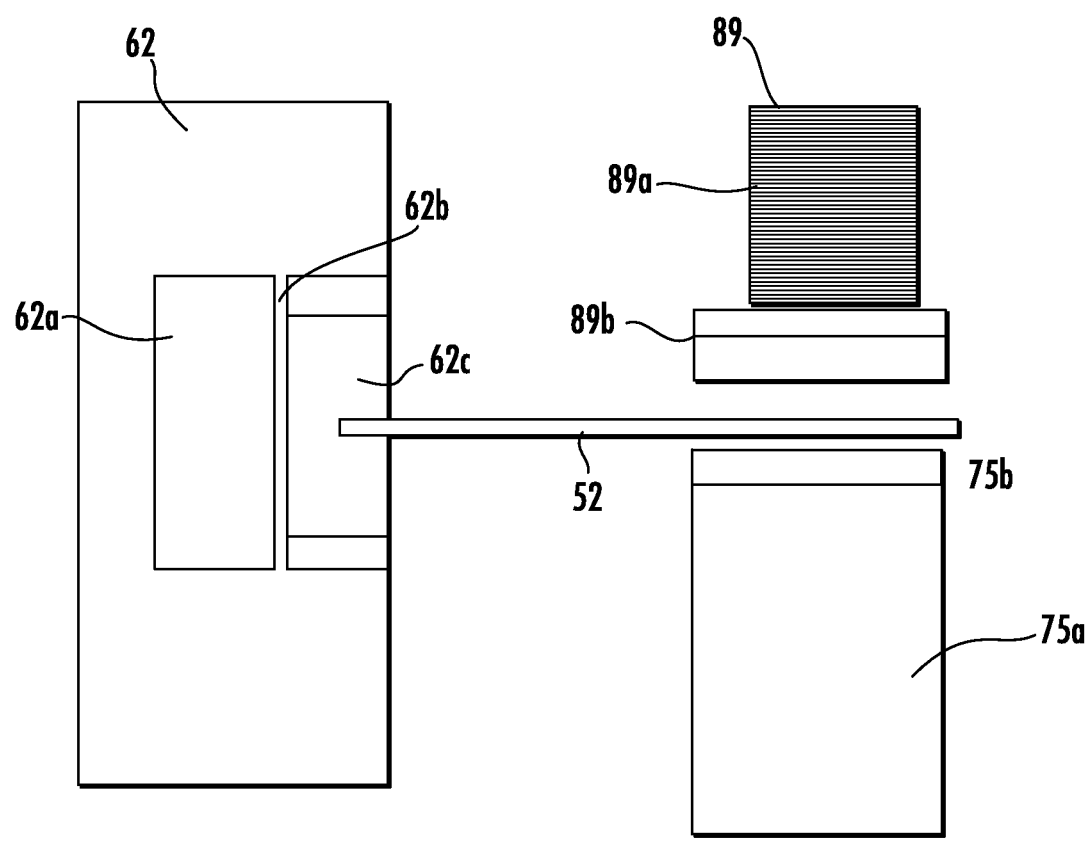
FIG. 8 is a schematic illustration of a second configuration of the device of FIG. 2, with a second engagement system.
Figure 9A:
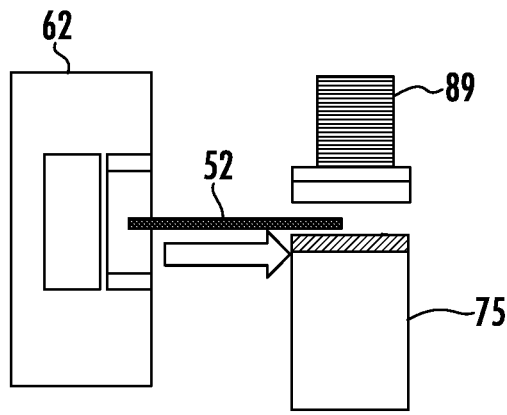
FIGS. 9A-9D are schematic illustrations of steps of engagement and operation of the device of FIG. 2.
Figure 9B:
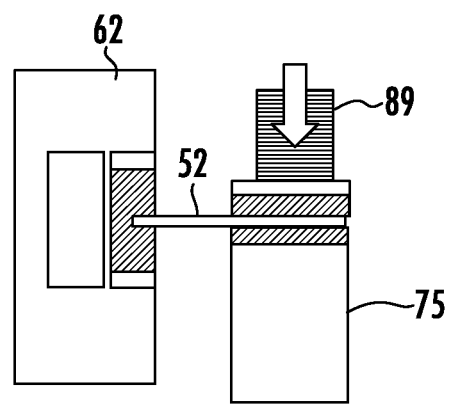
Figure 9C:
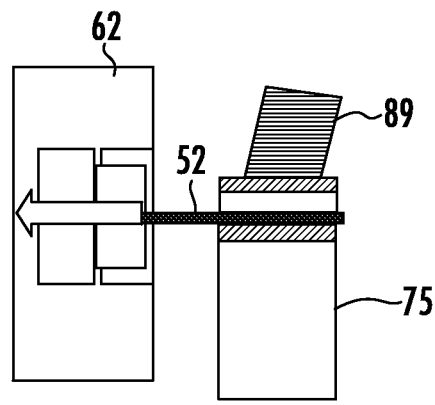
Figure 9D:
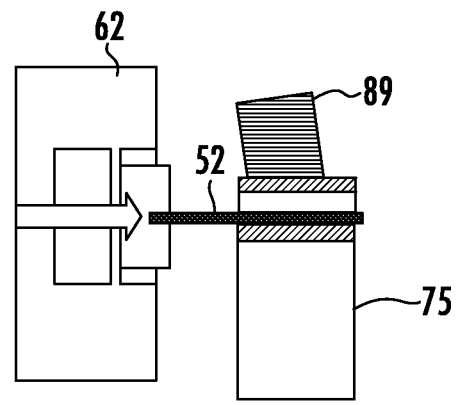

Illustrated in FIG. 8 is a variation embodiment of the engagement between the cantilever actuator 75 and the strap 52, which uses a system 89 for engagement of the permanent magnet 89b supported by a spring system 89a, which is also governed by a lever mechanism. Once the metal strap 52, which may be made of magnetic or nonmagnetic material, has been inserted, the magnet 89b is brought up to the strap 52 by acting on the lever mechanism, and presses the strap 52 itself against the end 89b of the actuator 75 made of ferromagnetic material, for example, nickel. Detachment of the strap 52 is obtained by acting on the lever mechanism. The magnet/lever mechanism ensemble may be easily replaced.

FIG. 9 shows in detail the coupling and operating steps, in a way similar to what is represented in FIG. 6. As may be noted, in this case the system 89 does not slide in an opposite direction with respect to the end 79b, on account of the magnetic coupling, but the spring 79a bends and is inclined, following the displacement of the strap 52.

Provided below are some reference values for the magnet engagement system 89. The permanent magnet 79b may be made, for example, of neodimium-iron-boron (of the Neo-Delta-Magnet type), associated to which is an energy product density of magnetic flux times force of the magnetic field=B×H=278 kJ/m³.

With a magnet 79b of dimensions 5×2.5×2 mm a force of 4.5 N is transmitted by the spring 79a, while the energy E is equal to 278×(5×2.5×2)×10E-9 kJ=6.95×10E-6 kJ=6.95 mJ. As may be seen, the value of the energy E is very low. The maximum force in the direction of displacement S is 2.7 N.

Also the magnet 79b has a nickel finish towards the strap 52, with the nickel-steel coefficient being 0.6. Since the magnetic field produced by permanent magnets may affect the behavior of electronic devices, preferably the fixed part 70 comprises steel shields, whereas the replaceable part 60 does not contain any sensitive component.

Figure 10:
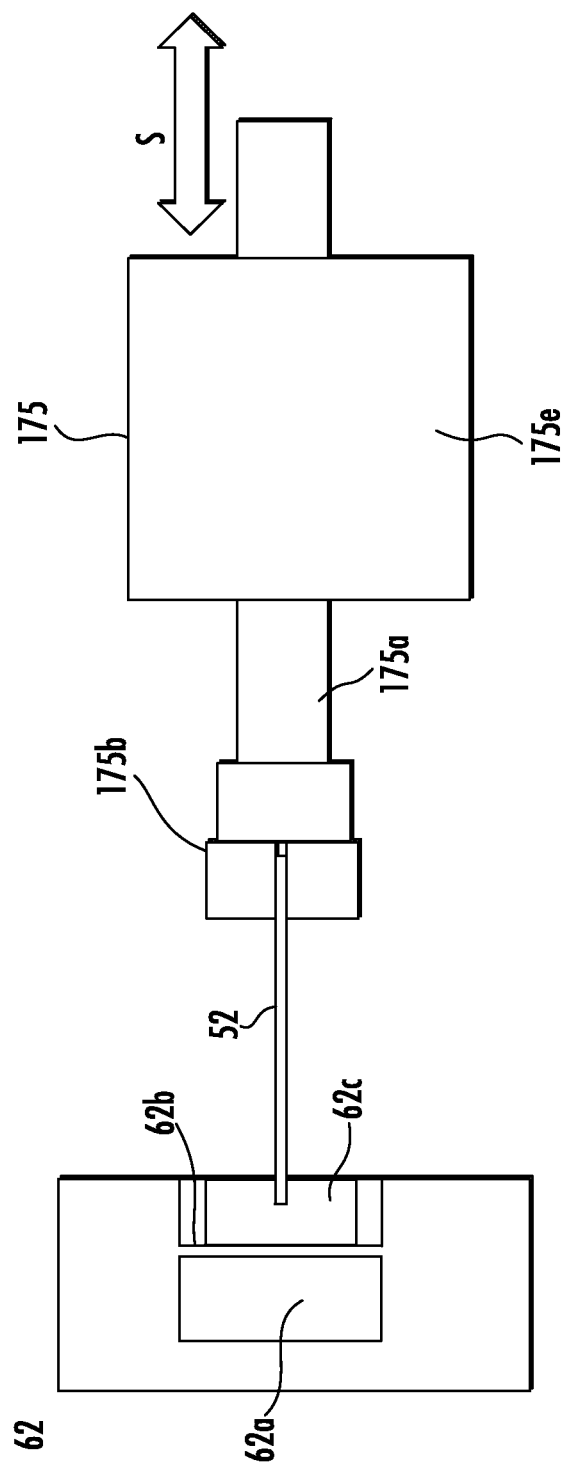
FIG. 10 is a schematic illustration of a detail of a variation of the device of FIG. 2, for dispensing a fluid using a second actuator and a third engagement system.

Illustrated in FIG. 10 is a linear actuator 175, which may also be of a piezoelectric type, and comprises a motor part 175e, which linearly displaces, along the axis S, a shaft 175a, which translates linearly in the direction of displacement S and is associated to the end of the strap 52 not associated to the membrane 62b, in particular via a cam coupling 175b.

Figure 11A:
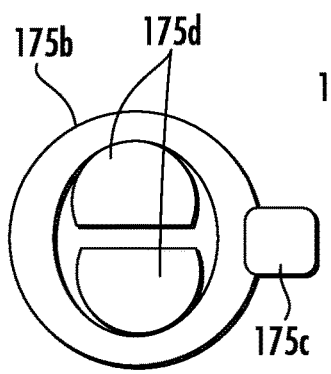
FIGS. 11A-11C and FIGS. 12A-12C are schematic views of the third engagement system of FIG. 10.
Figure 11B:
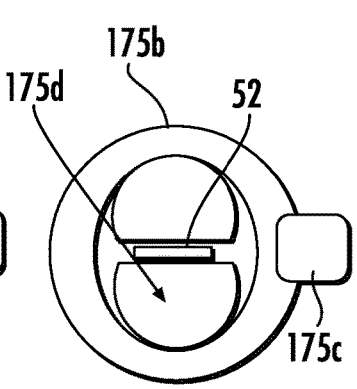
Figure 11C:
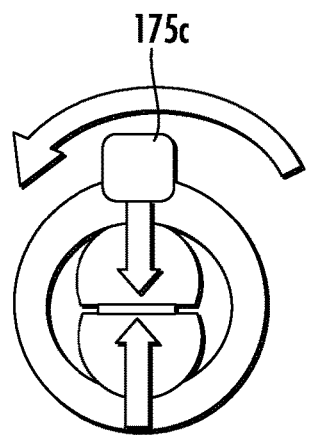
Figure 12A:
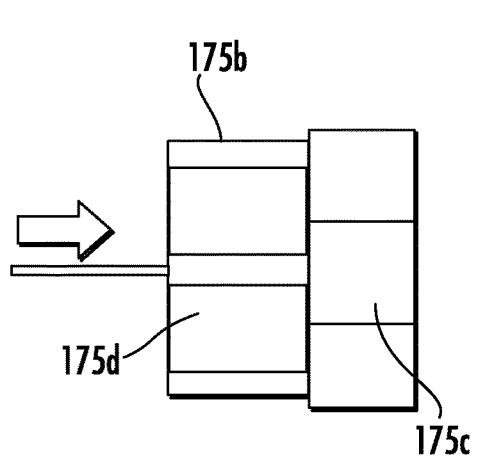
Figure 12B:
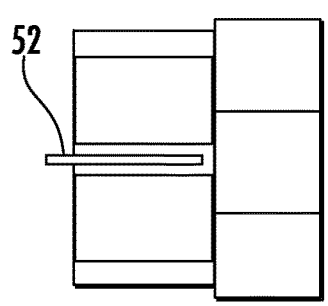
Figure 12C:
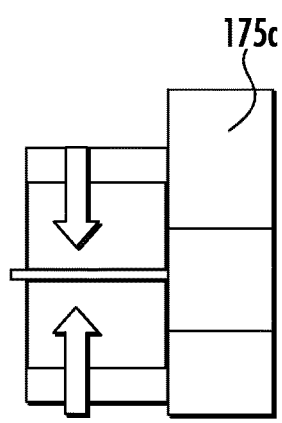

Represented in detail in FIG. 11 is the connection of the linear actuator 175 to the strap 52, obtained via the cam coupling 175b. The strap 52 is inserted in a space between two shaped jaws 175d and can slide along the perpendicular axis, parallel to the displacement S, on which an internal cam-shaped spindle 175c acts. FIG. 11A shows the cam coupling 175b in front view (the plane perpendicular to the direction of displacement S) without the strap 52. FIG. 11B shows the cam coupling 175b with the strap inserted between the jaws 175d, while FIG. 11C shows gripping of the strap 52. By acting on a lever, the spindle 175c turns and moves the two jaws 175d, thus blocking the lamina or strap 52. A spring enables the jaws 175d to open and release the lamina once the spindle has been turned into the original position. FIG. 12 shows the same configurations as those of FIG. 11 in lateral section.

Figure 13:
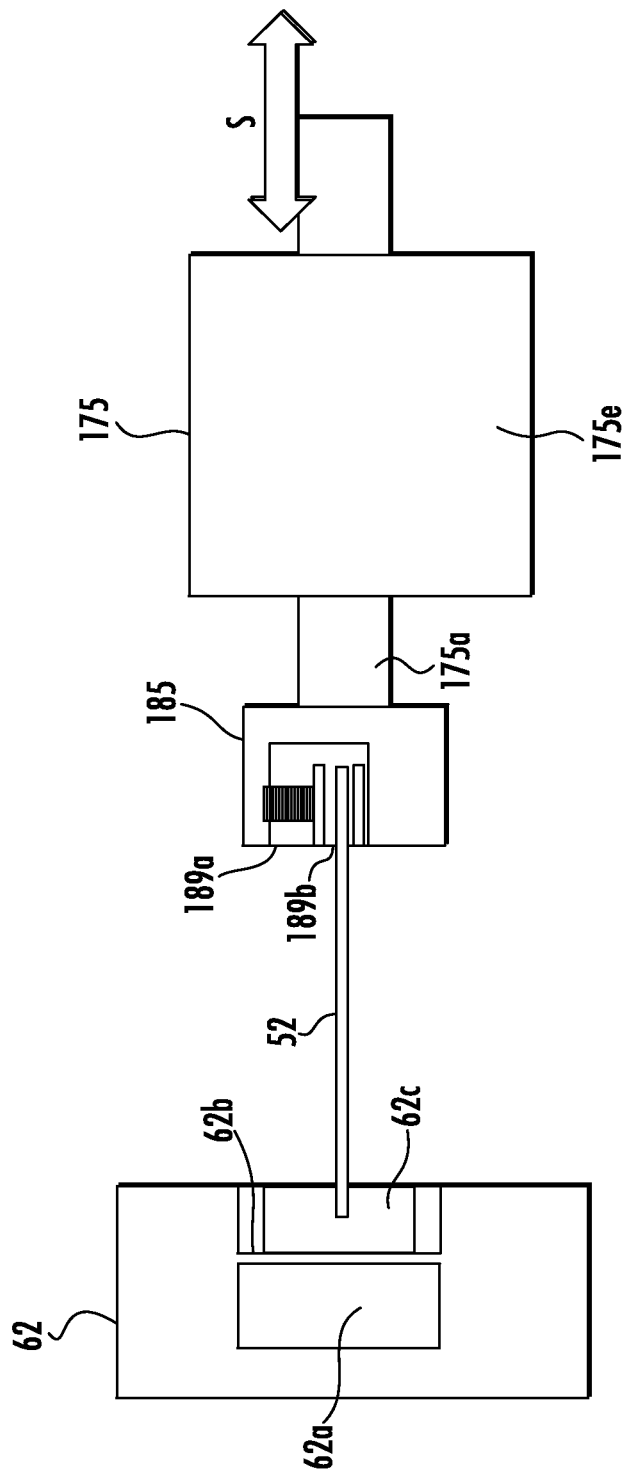
FIG. 13 shows the device of FIG. 10 using a further mode of engagement.

Also in the case of the linear actuator it is possible to use an alternative connection system 189 that uses a permanent magnet 189b supported by a spring 189a free to shift along the axis in order to compensate for the reciprocating motion of the strap 52. The engagement system 189 is illustrated in FIG. 13 inserted in a support 185 on the end of the shaft 175a, and substantially corresponds to the system 89 illustrated previously.

Figure 14:
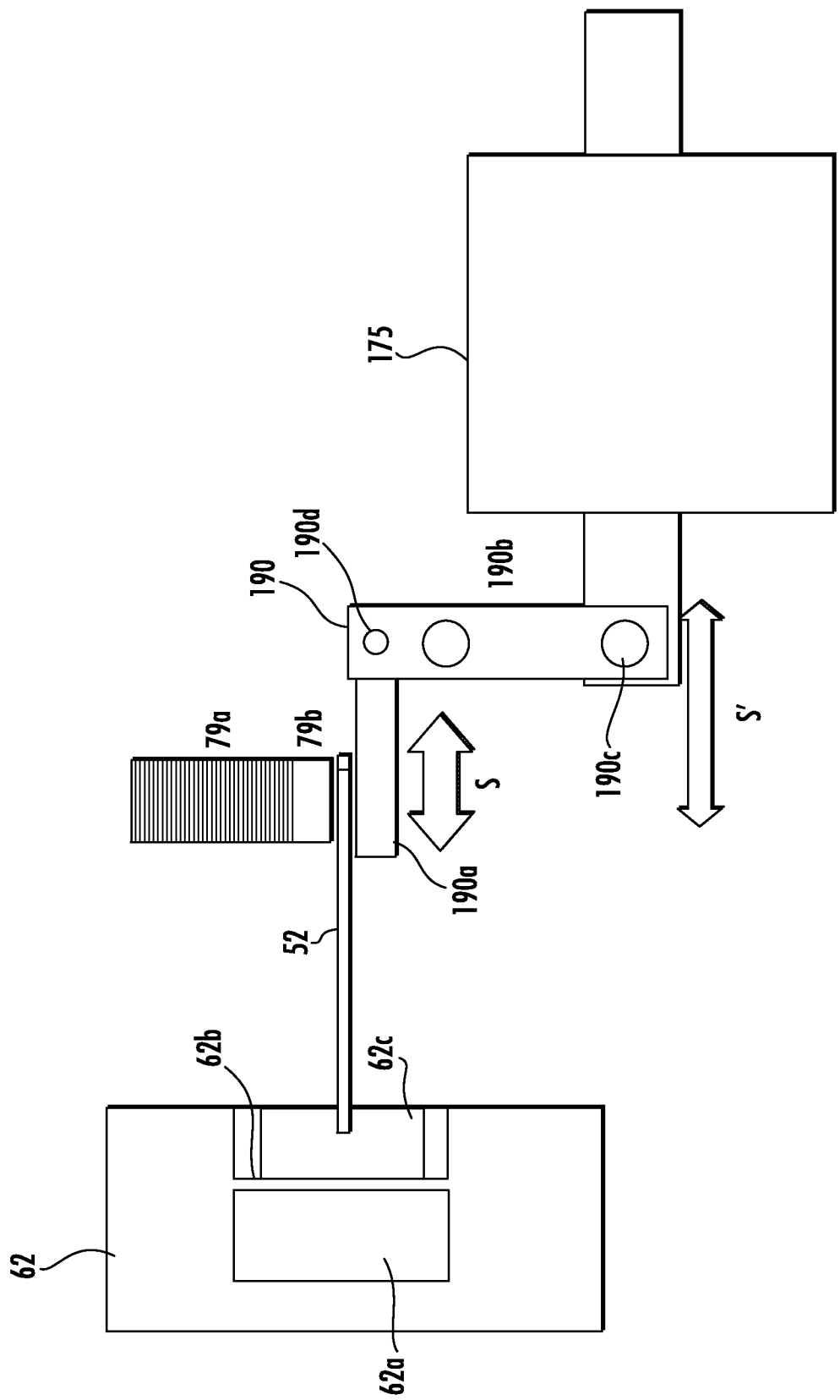
FIG. 14 shows the device of FIG. 10 using a device for reduction of motion.

Illustrated in FIG. 14 is a linear actuator 175 associated to a cantilever mechanism 190, operating as a rocker, in order to obtain a reduced range of displacement S of the strap 52 starting from a displacement S' of the linear actuator 175, and thus increase the force. The cantilever mechanism 190 comprises a vertical arm 190b and a horizontal arm 190a, which is associated in a rotatable way via a pin 190c to the vertical arm 190b. The shaft 175a is likewise connected, via a pin 190b, to the vertical arm 190d of the cantilever 190. The strap 52 is fixed on the horizontal arm 190a, substantially along the same longitudinal axis, and consequently the cantilever 190 provides a transmission with reduction of range of displacement of the linear actuator 175. The coupling of the cantilever mechanism 190 to the strap 52 is similar to that of the cantilever actuator 75, with the use of the pressing element 79 and with similar coefficients of friction. It is possible in this way to use linear piezoelectric actuators having a lower force and smaller dimensions. Connection to the pump may be made via the mechanical or magnetic system already illustrated for operation of the linear actuator 175.

The mechanical alignment between the fixed part 70 and the replaceable part 60 is guaranteed by conical pins moulded in the case of the replaceable part 60, which couple with corresponding holes in the fixed part 70.

Engagement between the two parts 60 and 70 is obtained with metal hooks moulded in the body of the fixed part 70. These hooks couple to corresponding eyelets on the replaceable part 60. Preferably, the hooks and the eyelets are configured in such a way that to remove the replaceable part 60 it is necessary to exert a tensile force, which leads to failure of the eyelets. In this way, re-use of a replaceable part that has already been mounted once is prevented. The battery 77 installed on the fixed part is of the AA type.

Hence, the advantages of the approaches described emerge clearly from the foregoing description. The device and the corresponding method described enable simplification of the production of the MEMS micro-pump, eliminating the integrated pressure sensor, which is transferred onto the fixed part. This enables elimination of elements such as bonding pads and internal connections and hence elimination of the exposed channel in so far as the inlet and outlet for the fluid can be located on the opposite faces of the pump. The fluid can be drawn in by the MEMS micro-pump on one side and pumped from the opposite side, thus simplifying production of the pump.

Furthermore, the device and the method described enable simplification of the replaceable part of the device, eliminating the actuator and the internal electrical connections (wire bonding), as well as external connection pads, with evident advantages from the standpoint of production and costs. The MEMS structure of the micro-pump is fixed directly on the structure.

In addition, the fixed control part is simplified, given that the spring contacts are eliminated. Moreover, given that the pressure sensor is moved in the fluid connection on the fixed part, the device described enables use of a standard MEMS for measuring the pressure.

Of course, without prejudice to the principle of the invention, the details and the embodiments may vary, even significantly, with respect to what has been described herein purely by way of example, without departing from the sphere of protection, this sphere of protection being defined in the annexed claims.

As an alternative to a micro-pump made of silicon, a micro-pump made of plastic may be installed, even though usually the latter presents lower performance.

That which is claimed is:

1. A device for dispensing a fluid comprising:
a fixed part to be worn by a user;
a fluid connection comprising a terminal outlet and a needle coupled to the terminal outlet for dispensing a fluid;
a replaceable part coupled to said fixed part via said fluid connection, and comprising
a reservoir for containing the fluid to be dispensed, and
a micro-pump coupled to said reservoir and configured to send the fluid to said fixed part through said fluid connection;
said fixed part comprising
an actuator configured to operate said micro-pump,
a pressure-sensor in proximity to the terminal outlet of said fluid connection and associated with dispensing the fluid from said needle, and
an electronic control module configured to control operation of said micro-pump via said pressure-sensor; and
a transmission member for transfer of motion that connects said actuator in said fixed part to said micro-pump in said replaceable part, with said micro-pump including a chamber and a mobile element for varying a volume of the chamber.

2. The device according to claim 1, wherein said transmission member comprises at least one of a lamina and a strap.

3. The device according to claim 2, wherein said lamina is coupled to said micro-pump, and further comprising an engagement system that is configured to receive said lamina inserted therein for engagement with said actuator.

4. The device according to claim 3, wherein said engagement system comprises a spring, and a pressing element pushed by said spring against a first surface of said lamina, with a second surface of said lamina opposite the first surface resting on said actuator.

5. The device according to claim 3, wherein said engagement system comprises a spring and a permanent magnet pushed by said spring against a first surface of said lamina, with a second surface of said lamina opposite the first surface resting on said actuator.

6. The device according to claim 1, wherein said actuator comprises a cantilever actuator.

7. The device according to claim 1, wherein said actuator comprises a linear actuator.

8. The device according to claim 1, wherein said micro-pump comprises an outlet conduit on a wall opposite a wall on which a fluid transfer connection is located which transfers the fluid to be dispensed from said reservoir to said micro-pump.

9. The device according to claim 1, wherein said micro-pump comprises an outlet conduit on a wall opposite a wall on which a fluid transfer connection is located which transfers the fluid to be dispensed from said reservoir to said micro-pump, wherein said transmission member and the outlet conduit are on the same wall.

10. The device according to claim 1, wherein said micro-pump comprises an outlet conduit on a wall opposite a wall on which a fluid transfer connection is located which transfers the fluid to be dispensed from said reservoir to said micro-pump, wherein said transmission member and the fluid transfer connection are on the same wall.

11. A device, for dispensing a fluid comprising:
a fixed part to be worn by a user;
a fluid connection comprising a terminal outlet and a needle coupled to the terminal outlet for dispensing a fluid;
a replaceable part coupled to said fixed part via said fluid connection, and comprising
a reservoir for containing the fluid to be dispensed, and
a micro-pump coupled to said reservoir and configured to send the fluid to said fixed part through said fluid connection;
an actuator configured to operate said micro-pump; and
said fixed part comprising
a pressure-sensor in proximity to the terminal outlet of said fluid connection and associated with dispensing the fluid from said needle, and
an electronic control module configured to control operation of said micro-pump via said pressure-sensor, wherein said micro-pump comprises an outlet conduit on a wall opposite a wall on which a fluid transfer connection is located which transfers the fluid to be dispensed from said reservoir to said micro-pump, wherein said fixed part comprises a hydraulic circuit and a needle system, with said outlet conduit being coupled to said hydraulic circuit via said needle system, and said replaceable part comprising a fluid-tight diaphragm that is perforated by said outlet conduit.

12. A device for dispensing a fluid comprising:
a fixed part to be worn by a user and comprising an actuator;
a fluid connection comprising a terminal outlet and a needle coupled to the terminal outlet for dispensing a fluid;
a replaceable part coupled to said fixed part via said fluid connection, and comprising
a reservoir for containing the fluid to be dispensed, and
a MEMS configured micro-pump coupled to said reservoir and operated autonomously by said actuator to send the fluid to said fixed part through said fluid connection; and
said fixed part comprising
a pressure-sensor adjacent the terminal outlet of said fluid connection, and
a control module configured to control operation of said micro-pump via said pressure-sensor.

13. The device according to claim 12, further comprising a transmission member for transfer of motion that connects said actuator to said micro-pump, with said micro-pump including a chamber and a mobile element for varying a volume of the chamber.

14. The device according to claim 12, wherein said actuator comprises at least one of a cantilever actuator and a linear actuator.

15. The device according to claim 12,
further comprising an engagement system that is configured to engage said actuator, with said engagement system comprising a spring, and a pressing element pushed by said spring against a first surface of a transmission member, with a second surface of said transmission member opposite the first surface resting on said actuator.

16. The device according to claim 12, further
comprising an engagement system that is configured to engage said actuator, with said engagement system comprising a spring and a permanent magnet pushed by said spring against a first surface of a transmission member, with a second surface of said transmission member opposite the first surface resting on said actuator.

17. A method for controlling fluid to be dispensed from a device to be worn by a user, the method comprising:
providing a fixed part to be worn by the user;
providing a fluid connection comprising a terminal outlet and a needle coupled to the terminal outlet for dispensing the fluid;
providing a replaceable part coupled to the fixed part via the fluid connection, the replacement part comprising a reservoir containing the fluid to be dispensed, and a micro-pump coupled to the reservoir to send the fluid to the fixed part through the fluid connection, with the micro-pump being operated via an actuator; and the fixed part comprising the actuator, a pressure-sensor in proximity to the terminal outlet of the fluid connection and associated with dispensing the fluid from the needle, and an electronic control module controlling operation of the micro-pump via the pressure-sensor; and
providing a transmission member for transfer of motion that connects the actuator to the micro-pump, with the micro-pump including a chamber and a mobile element for varying a volume of the chamber.

18. The method according to claim 17, wherein
the transmission member comprises a lamina coupled to the micro-pump, and further comprising providing an engagement system to receive the lamina inserted therein for engagement with the actuator.

19. The method according to claim 18, wherein
the engagement system comprises a spring, and a pressing element pushed by the spring against a first surface of the lamina, with a second surface of the lamina opposite the first surface resting on the actuator.

20. The method according to claim 18, wherein
the engagement system comprises a spring and a permanent magnet pushed by the spring against a first surface of the lamina, with a second surface of the lamina opposite the first surface resting on the actuator.

21. The method according to claim 17, wherein
the micro-pump comprises an outlet conduit on a wall opposite a wall on which a fluid transfer connection is located which transfers the fluid to be dispensed from the reservoir to the micro-pump.

22. A method, for controlling fluid to be dispensed from a device to be worn by a user, the method comprising:
providing a fixed part to be worn by the user;
providing a fluid connection comprising a terminal outlet and a needle coupled to the terminal outlet for dispensing the fluid;
providing a replaceable part coupled to the fixed part via the fluid connection, the replacement part comprising a reservoir containing the fluid to be dispensed, and a micro-pump coupled to the reservoir to send the fluid to the fixed part through the fluid connection, with the micro-pump being operated via an actuator; and the fixed part comprising a pressure-sensor in proximity to the terminal outlet of the fluid connection and associated with dispensing the fluid from the needle, and an electronic control module controlling operation of the micro-pump via the pressure-sensor, wherein the micro-pump comprises an outlet conduit on a wall opposite a wall on which a fluid transfer connection is located which transfers the fluid to be dispensed from the reservoir to the micro-pump, and wherein the fixed part comprises a hydraulic circuit and a needle system, with the outlet conduit coupled to the hydraulic circuit via the needle system, and the replaceable part comprising a fluid-tight diaphragm that is perforated by the outlet conduit.

23. The method according to claim 17, further comprising
controlling the fluid being dispensed based on a function of a drop in pressure measured by the pressure-sensor on the fluid connection downstream of an outlet conduit of the micro-pump in proximity of the attachment of the fluid connection with the needle.

* * * * *